United States Patent [19]

Matsutani

[11] Patent Number: 4,700,043

[45] Date of Patent: Oct. 13, 1987

[54] METHOD OF FORMING BORE IN EYELESS OPERATING NEEDLE

[75] Inventor: Kanji Matsutani, Takanezawa, Japan

[73] Assignee: Matsutani Seisakusho Co., Ltd., Tochigi, Japan

[21] Appl. No.: 939,702

[22] Filed: Dec. 9, 1986

[51] Int. Cl.4 .................... B23K 26/00; B23K 15/00
[52] U.S. Cl. ................... 219/121 LJ; 128/339; 163/5; 219/121 EK
[58] Field of Search ............ 219/121 LH, 121 LJ, 219/121 EJ, 121 EK; 163/1, 5; 128/339; 223/102; 66/116, 122; 112/224, 222

[56] References Cited

U.S. PATENT DOCUMENTS

| | | | |
|---|---|---|---|
| 3,038,475 | 6/1962 | Orcutt | 128/339 |
| 3,835,912 | 9/1974 | Kristensen et al. | 128/339 X |
| 4,081,655 | 3/1978 | Gale | 219/121 LJ |
| 4,159,686 | 7/1979 | Heim | 163/5 X |
| 4,501,312 | 2/1985 | Matsutani | 163/5 |

Primary Examiner—C. L. Albritton
Attorney, Agent, or Firm—Kane, Dalsimer, Kane, Sullivan and Kurucz

[57] ABSTRACT

A method of forming a bore for attachment of an end of a suture, in a proximal end portion of an eyeless operating needle. An original needle is prepared which has its outer diameter greater than that of the operating needle. Beam is applied to an end face of a proximal end portion of the original needle to form the bore therein extending along an axis of the proximal end portion of the original needle, with an outer peripheral portion of the original needle serving as a heat conductive material. Subsequently, an outer diameter of the original needle is reduced to remove the outer peripheral portion from the original needle, to form the operating needle. Alternatively, a separate heat conductive material is disposed around at least one eyeless operating needle and is removed after the bore is formed in the proximal end portion of the operating needle.

14 Claims, 11 Drawing Figures

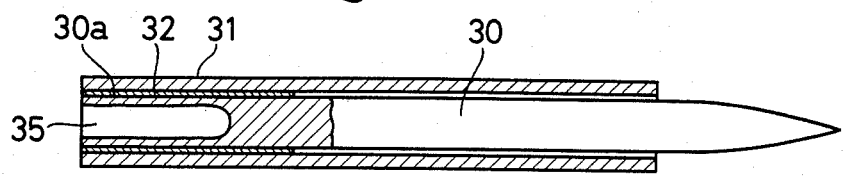
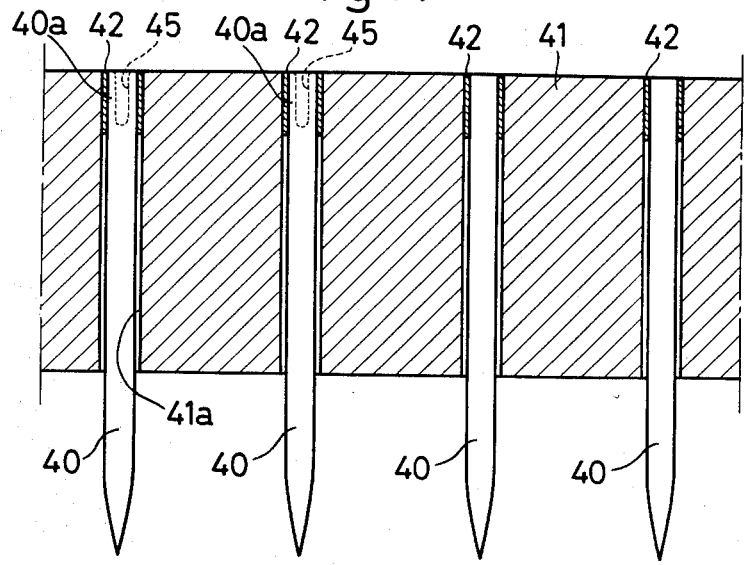
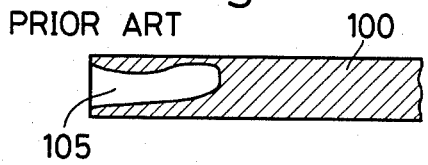
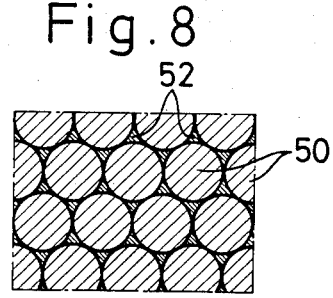
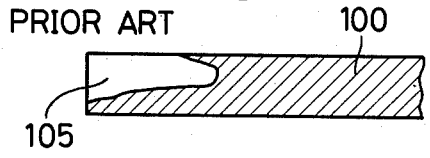
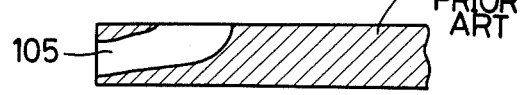

METHOD OF FORMING BORE IN EYELESS OPERATING NEEDLE

BACKGROUND OF THE INVENTION

The present invention relates to a method of forming a bore for attachment of a suture, in a proximal end portion of an eyeless operating needle.

An eyeless operating needle has a proximal end portion formed therein with a bore of a predetermined depth extending along the axis of the needle. An end of a suture is inserted into the bore and, subsequently, the proximal end portion of the needle is staked, to thereby attach the suture to the needle.

There are various manners of forming the bore, such as, for example, a drilling machining, electric discharge machining, laser beam machining, electron beam machining and the like. When the needle is particularly small in diameter, machinings are employed which utilize a beam energy such as laser, electron or the like, in which the material of the needle is sublimated by the beam energy to form a bore therein. Various improvements have been proposed with respect to such machinings using the beam energy, as has been disclosed in Japanese Patent Application Laid-Open Nos. 52-111294, 60-170590 and 60-184485, Japanese Utility Model Publication No. 56-37918, Japanese Utility Model Application Laid-Open No. 55-43691 and the like.

However, in case where the needle is small in outer diameter and the wall thickness surrounding the bore formed in the proximal end portion of the needle is thin, for example, when a bore is formed, by the beam energy, in a needle which is used in brain operations or the like, a rate or percentage of occurrence of defective needles has been very high, in which a bore 105 is bent with respect to a center axis of a needle 100 as shown in FIG. 9 of the accompanying drawings, or a part of a wall surrounding a bore 105 is destroyed as shown in FIGS. 10 and 11.

The inventor of the present application has considered and presumed causes of the occurrence of the above-noted defects as follows. That is, the beam is a pulse of short time duration on the order of 0.001 second, but the inside of the wall surrounding the bore is brought to a high temperature on the order of 10,000° C. Moreover, there is almost no heat radiation or diffusion, because the outside of the wall is air which is low in thermal conductivity. Accordingly, the wall must have its thickness sufficient to withstand the given heat energy. For example, however, when the center of the beam is not coincident with the center of the end face of the proximal end portion of the needle, a specific portion of the wall surrounding the bore becomes further thin, and the wall thickness of the specific portion would be brought to a level lower than the limitative thickness. In addition, if the energy distribution of the beam is deviated, the wall thickness of a portion to which the heat energy is concentrated is brought to a level lower than the allowable level. The inventor has presumed, this would result in the occurrence of the above-mentioned defective needles.

OBJECT AND SUMMARY OF THE INVENTION

It is an object of the present invention to provide a method of forming a bore for attachment of an end of a suture, in a proximal end portion of an eyeless operating needle, which method can prevent the bore from being bent and can prevent a wall surrounding the bore from being destroyed.

According to the invention, there is provided a method of forming a bore for attachment of an end of a suture, in a proximal end portion of a metallic eyeless operating needle, the bore extending along an axis of the proximal end portion, the method comprising the steps of:

with a heat conductive material being disposed around at least the proximal end portion of the operating needle, applying a beam to an end face of the proximal end portion to form the bore therein; and subsequently, removing the heat conductive material from the operating needle.

BRIEF DESCRIPTION OF THE DRAWINGS

FIG. 6 is a cross-sectional view showing a third embodiment of the invention in which an eyeless operating needle is surrounded by a separate heat conductive material subsequently to be removed from the operating needle;

FIG. 7 is a cross-sectional view showing a fourth embodiment of the invention in which a plurality of eyeless operating needles are surrounded by a separate heat conductive material subsequently to be removed from the needles;

FIG. 8 is a cross-sectional view showing a fifth embodiment of the invention, in which a plurality of eyeless operating needles are bundled together by a solder, and the needles adjacent a specific one to which a beam is applied to form a bore therein serve as a heat conductive material; and Figs. 9 through 11 are fragmental cross-sectional views respectively showing defective needles manufactured in accordance with the prior art methods.

DETAILED DESCRIPTION

Various embodiments of the invention will be described in detail with reference to FIGS. 1 through 8 of the accompanying drawings. In these figures, a longitudinally intermediate portion of each needle is omitted, and a diameter of the needle with respect to its length is largely shown than its actual diameter.

Figure 1:
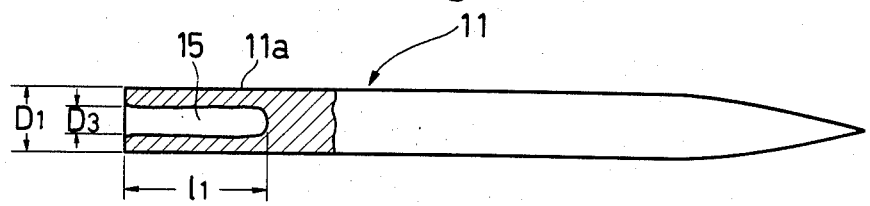
FIG. 1 is a partially cross-sectional, enlarged side elevational view showing an original needle to which a first step of a method in accordance with a first embodiment of the invention has been applied to form a bore in a proximal end portion of the needle.
Figure 2:
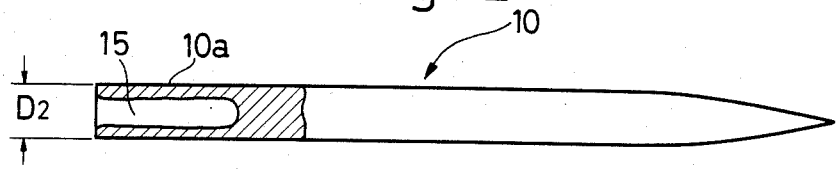
FIG. 2 is a view similar to FIG. 1, but showing a completed eyeless operating needle manufactured by removing an outer peripheral portion serving as a heat conductive material, from the original needle shown in FIG. 1.

FIGS. 1 and 2 show a first embodiment of the invention. In this embodiment, as shown in FIG. 1, an original stainless steel needle 11 formed straight is first prepared which has an outer diameter $D_1$ of 0.26 mm, for example, greater than that $D_2$ of a finally obtained, eyeless operating needle 10 shown in FIG. 2. A laser beam is applied to a center of an end face of a proximal end portion 11a of the original needle 11, to form a bore 15 which extends along an axis of the proximal end portion 11a and which has an inner diameter $D_3$ of 0.13 mm and an effective depth $l_1$ of 0.8 mm.

Subsequently, the original needle 11 formed therein with the bore 15 is dipped, for 4 minutes, in an etching solution of 95° C. to 105° C. consisting of aqua regia, surface active agent and water, to gradually etching-grind the outer peripheral surface of the original needle 11, to thereby reduce the outer diameter thereof. Thus, as shown in FIG. 2, the eyeless operating needle 10 is manufactured which has the outer diameter $D_2$ of 0.23 mm and has the bore 15 formed in a proximal end portion 10a.

When a bore of 0.13 mm is formed in a needle having an outer diameter of 0.23 mm in accordance with the prior art methods described previously, the percentage of needles of good quality to the entire needles machined was 45%, whereas according to the above-described first embodiment, the percentage of needles of good quality was 79%.

The rise in the percentage of the needles of good quality is presumed to be due to the following reasons. That is, because the original needle 11 is relatively large in diameter, when the bore 15 is formed by means of the laser beam, the wall surrounding the bore 15 becomes thicker than the case of the prior art methods. Consequently, if the center of the laser beam is slightly shifted from the center of the end face of the proximal end portion 11a, the wall surrounding the bore is not reduced in thickness to a level lower than the limitative value and, in addition, if the energy distribution of the laser beam is slightly deviated, the heat energy with respect to the wall does not exceeds the allowable level.

The outer peripheral portion of the original needle 11 functions or serves as a heat conductive material for absorbing the heat energy from the wall to be formed around the bore 15 during the machining thereof.

The straight needle 11 obtained as described above is then bent and, subsequently, one end of a suture (not shown) is inserted into the bore 15. Then, the proximal end portion 10a is staked, to attach the suture to the needle 10.

The above-described etching is suitable for the reduction in diameter on the order of 0.01 to 0.05 mm. A second embodiment to be described below in connection with FIGS. 3 through 5 is highly efficient for the reduction in diameter greater than that by the above etching.

Figure 3:
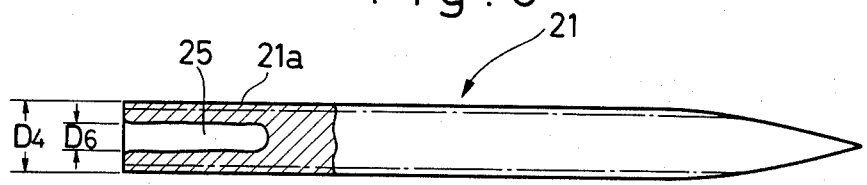
FIGS. 3 through 5 are views similar to FIGS. 1 and 2, but showing steps of a method in accordance with a second embodiment of the invention.
Figure 5:
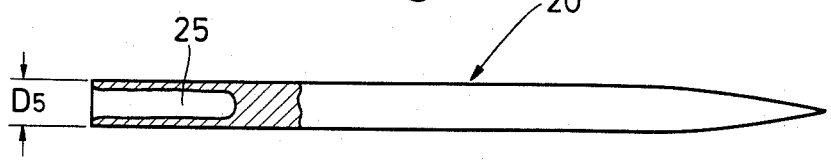

In the second embodiment, as shown in FIG. 3, an original stainless steel needle 21 is first prepared which has an outer diameter $D_4$ of 0.45 mm, for example, greater than that $D_5$ of a finally obtained, eyeless operating needle 20 shown in FIG. 5. Laser beam is applied to a center of an end face of a proximal end portion 21a of the original needle 21, to form a bore 25 having an inner diameter $D_6$ of 0.22 mm and extending along an axis of the proximal end portion 21a.

Figure 4:
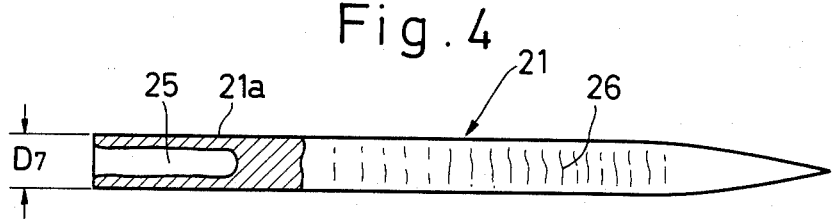

Subsequently, the outer diameter of the original needle 21 is reduced to an outer diameter $D_7$ of 0.335 mm as shown in FIG. 4, by means of a grinding such as a centerless machining. The centerless machining is generally known as a grinding method for rod-like materials. In case where the centerless machining is applied to the grinding of the above-noted original needle, a plate is arranged between a pair of columnar grindstones; the original needle 21 rests on an upper edge of the plate; and one of the grindstones is rotated at a relatively low speed, and the other grindstone is rotated at high speed in a direction opposite to the direction of rotation of the one grindstone, to grind the original needle 21 while rotating the same.

When the above centerless machining is done with respect to the original needle 21, a mark pattern 26 is formed on the outer peripheral surface of the original needle 21 as shown in FIG. 4. In view of this, a barrel machining or finishing is subsequently done with respect to the needle 21 to remove the mark pattern 26 therefrom. Thus, the eyeless operating needle 20 shown in FIG. 5 is obtained, which is mirror-finished in peripheral surface and has the outer diameter $D_5$ of 0.33 mm. What is the barrel machining is that works and a large number of balls are received in a polygonal barrel, and the barrel is rotated to bring the balls and the works into grinding contact with each other, to grind the works. In the second embodiment, two steps of grinding are carried out, including a first step of barrel grinding using ceramic balls and a second step of barrel grinding using steel balls. For the second embodiment, the percentage of needles of good quality was 93%.

FIG. 6 shows a third embodiment of the invention, in which a stainless steel, eyeless operating needle 30 having an outer diameter of 0.23 mm is inserted into a stainless steel pipe 31 having an inner diameter of 0.28 mm and an outer diameter of 0.5 mm. The needle 30 and the pipe 31 are heated to allow a solder 32 having its thermal conductivity approximate to that of the stainless steel, to flow into a gap between the needle 30 and the pipe 31. Then, the solder 32 is solidified to bring the needle 30 and the pipe 31 together. It is sufficient if the solder 32 is interposed only between a proximal end portion 30a of the needle 30 and the pipe 31. In addition, it may be considered that the solder 32 is previously deposited on the peripheral surface of the proximal end portion 30a of the needle 30, and the needle 30 is inserted into the pipe 31 which is under heated condition, to thereby fill the solder 32 into the gap between the needle 30 and the pipe 31. The solder 32 is thickly illustrated in FIG. 6 than its actual thickness.

Then, a laser beam is applied to an end face of the proximal end portion 30a of the needle 30 to form therein a bore 35 having a diameter of 0.13 mm. Subsequently, the needle 30 and the pipe 31 are heated to melt the solder 32, and the needle 30 is drawn out of the pipe 31. In addition, the solder 32 is removed from the needle 30.

In case of the third embodiment, the percentage of needles of good quality was 92%. In the third embodiment, the solder 32 and the pipe 31 serve as a heat conductive material for absorbing the heat from the wall surrounding the bore 35.

FIG. 7 shows a fourth embodiment of the invention, in which a plurality of stainless steel, eyeless operating needles 40 are inserted respectively into a plurality of through bores 41a each having a diameter of 0.28 mm and formed in a metallic table 41 in the form of a plate. Each of the needles 40 is fixedly secured, by means of solder 42, into a corresponding one of the through bores 41a. Then, laser beam is successively applied to end faces of proximal end portions 40a of the respective needles 40, to successively form bores 45 having a diameter of 0.13 mm, in the respective proximal end portions 40a. Subsequently, the table 41 is heated to melt the solder 42 to allow the needles 40 to be drawn out of the table 41. It was possible also for the fourth embodiment to obtain the percentage of needles of good quality which reaches 92%. In the fourth embodiment, the solder 42 and the table 41 serve as a heat conductive material for absorbing the heat from the wall surrounding the bore 45.

Moreover, in FIG. 7, when bores each having a diameter of 0.17 mm were formed respectively in needles each having an outer diameter of 0.23 mm, the percentage of needles of good quality was 46%. It is impossible for the prior art methods to form such bores.

FIG. 8 shows a fifth embodiment of the invention, in which a large number of stainless steel, eyeless operating needles 50 each having an outer diameter substantially equal to that of each needle shown in FIG. 7 are bundled together. The bundles 50 are dipped in a solder 52 under molten condition, with proximal end portions of the respective needles 50 being directed downwardly. After drawing the bundled needles 50 out of the solder bath, the solder 52 is solidified to obtain an assembly shown in FIG. 8. Laser beam is successively applied to end faces of proximal end portions of the respective needles 50 to successively form bores in the respective proximal end portions. In the fifth embodiment, during the application of the laser beam to a specific one of the needles 50 to form a bore therein, the solder 52 and the needles 50 adjacent the specific needle serve as a heat conductive material for absorbing heat from the wall surrounding the bore. After the completion of the formation of the bores in the entier needles 50, the solder 52 is molten to allow the needles 50 to be singly separated from each other.

It will be appreciated by one skilled in the art that, in all of the above-described embodiments, en electron beam may be used in substitution for the laser beam.

What is claimed is:

1. A method of forming a bore for attachment of an end of a suture, in a proximal end portion of a metallic eyeless operating needle, the bore extending along an axis of the proximal end portion, said method comprising the steps of:
    with a heat conductive material being disposed around at least the proximal end portion of the operating needle, applying a beam to an end face of the proximal end portion to form said bore therein; and
    subsequently, removing said heat conductive material from said operating needle.

2. A method as defined in claim 1, including the steps of:
    preparing a metallic original needle having its outer diameter greater than that of said operating needle, with an outer peripheral portion of said original needle serving as said heat conductive material;
    applying the beam to an end face of a proximal end portion of said original needle to form said bore therein; and
    subsequently, reducing the outer diameter of said original needle to remove said outer peripheral portion serving as said heat conductive material.

3. A method as defined in claim 2, including the step of:
    dipping said original needle in an etching solution to reduce the outer diameter thereof.

4. A method as defined in claim 2, including the step of:
    grinding said original needle to reduce the outer diameter thereof.

5. A method as defined in claim 4, including the steps of:
    grinding said original needle by a centerless machining; and
    subsequently, finishing said original needle by a barrel machining, to reduce the outer diameter of said original needle.

6. A method as defined in claim 1, wherein said heat conductive material disposed around the operating needle includes a metallic material lower in melting point than the operating needle.

7. A method as defined in claim 6, wherein the operating needle is formed of stainless steel, and said metallic material is a solder having its thermal conductivity approximate to that of the stainless steel.

8. A method as defined in claim 1, including the steps of:
    inserting the operating needle into a metallic pipe;
    filling metallic material into a gap between said pipe and at least the proximal end portion of the operating needle, the metallic material being lower in melting point than the operating needle and said pipe, said metallic material and said pipe serving as said heat conductive material;
    applying the beam to the end face of the proximal end portion of the operating needle to form the bore therein; and
    subsequently, melting said metallic material to draw the operating needle out of said pipe.

9. A method as defined in claim 1, including the steps of:
    preparing a metallic table having therein a plurality of inserting through bores;
    preparing a plurality of eyeless operating needles;
    inserting each of the operating needles into a corresponding one of said through bores in said table;
    filling a metallic material into respective gaps between the operating needles and said through bores in said table, said metallic material being lower in melting point than the operating needle and said table, said metallic material and said table serving as said heat conductive material;
    applying the beam successively to end faces of proximal end portions of the respective operating needles to form bores in the respective proximal end portions; and
    subsequently, melting said metallic material to draw said operating needles out of the respective through bores in said table.

10. A method as defined in claim 1, including the steps of:
    preparing a plurality of eyeless operating needles;
    bundling together said operating needles;
    filling a metallic material into gaps between the bundled operating needles, the metallic material being lower in melting point than the operating needles;
    applying the beam successively to end faces of proximal end portions of the bundled respective operating needles to successively form the bores in the respective proximal end portions, wherein during the application of the beam to a specific one of the bundled operating needles, the operating needles adjacent the specific needle and the metallic material serve as said heat conductive material; and
    melting the metallic material to singly separate the operating needles from each other.

11. A method as defined in claim 1, wherein said beam is a laser beam.

12. A method as defined in claim 1, wherein said beam is an electron beam.

13. A method of manufacturing an eyeless operating needle having a proximal end portion formed therein with a bore for attachment of an end of a suture, the bore extending along an axis of the proximal end portion, said method comprising the steps of:

preparing an original needle having its outer diameter greater than that of the operating needle;

applying a beam to an end face of a proximal end portion of said original needle to form said bore in the proximal end portion of the original needle, with an outer peripheral portion of said original needle serving as a heat conductive material; and reducing an outer diameter of said original needle to remove the outer peripheral portion, to form said eyeless operating needle.

14. A method of manufacturing an eyeless operating needle having a proximal end portion formed therein with a bore for attachment of an end of a suture, the bore extending along an axis of the proximal end portion, said method comprising the steps of:

preparing at least one eyeless operating needle;

disposing a separate heat conductive material around at least the proximal end portion of the operating needle;

applying a beam to an end face of the proximal end portion of the operating needle to form said bore in the proximal end portion, and removing said heat conductive material from the operating needle.

* * * * *